United States Patent
Hoppe et al.

(10) Patent No.: US 9,359,205 B2
(45) Date of Patent: Jun. 7, 2016

(54) PRODUCTION OF TRISILYLAMINE FROM MONOCHLOROSILANE AND AMMONIA BY USE OF INERT SOLVENT

(71) Applicants: Carl-Friedrich Hoppe, Gruendau (DE); Hartwig Rauleder, Rheinfelden (DE); Christian Goetz, Seligenstadt (DE)

(72) Inventors: Carl-Friedrich Hoppe, Gruendau (DE); Hartwig Rauleder, Rheinfelden (DE); Christian Goetz, Seligenstadt (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/724,114

(22) Filed: May 28, 2015

(65) Prior Publication Data

US 2015/0259207 A1 Sep. 17, 2015

Related U.S. Application Data

(63) Continuation of application No. 14/344,793, filed as application No. PCT/EP2012/071873 on Nov. 6, 2012.

(30) Foreign Application Priority Data

Dec. 16, 2011 (DE) .......................... 10 2011 088 814

(51) Int. Cl.
| | | |
|---|---|---|
| *C01B 33/00* | (2006.01) | |
| *C07F 7/02* | (2006.01) | |
| *C01B 21/087* | (2006.01) | |
| *B01D 3/14* | (2006.01) | |
| *B01D 3/00* | (2006.01) | |
| *B01J 19/24* | (2006.01) | |

(52) U.S. Cl.
CPC .............. *C01B 21/087* (2013.01); *B01D 3/009* (2013.01); *B01D 3/143* (2013.01); *B01J 19/24* (2013.01); *C01B 33/00* (2013.01); *C07F 7/025* (2013.01); *B01J 2219/00002* (2013.01); *B01J 2219/24* (2013.01)

(58) Field of Classification Search
CPC ............................... C01B 21/087; B01J 19/24
USPC ........................................... 556/410; 423/324
See application file for complete search history.

(56) References Cited

U.S. PATENT DOCUMENTS

| | | | |
|---|---|---|---|
| 6,528,658 B1 | 3/2003 | Miura et al. | |
| 2010/0310443 A1* | 12/2010 | Miller | .................... B01J 4/002 423/324 |
| 2011/0136347 A1 | 6/2011 | Kovarsky et al. | |
| 2013/0323151 A1 | 12/2013 | Mueh et al. | |
| 2014/0072497 A1 | 3/2014 | Doering et al. | |

FOREIGN PATENT DOCUMENTS

| | | | |
|---|---|---|---|
| EP | 1 074 537 | 2/2001 | |
| WO | WO 2010/141551 A1 | 12/2010 | |
| WO | 2011 049811 | 4/2011 | |
| WO | WO 2011049811 A2 * | 4/2011 | ............ C01B 21/087 |

OTHER PUBLICATIONS

International Search Report Issued Jan. 25, 2013 in PCT/EP12/071873 Filed Nov. 6, 2012.
International Search Report issued Jan. 25, 2013 in Corresponding PCT/EP2012/071873 (with English Translation of Category of Cited Documents).

* cited by examiner

*Primary Examiner* — Porfirio Nazario Gonzalez
*Assistant Examiner* — Kofi Adzamli
(74) *Attorney, Agent, or Firm* — Oblon, McClelland, Maier & Neustadt, L.L.P.

(57) ABSTRACT

The present invention relates to a specific process for producing trisilylamine from monochlorosilane and ammonia in the liquid phase. The invention further relates to a plant wherein such a process can be carried out with advantage.

9 Claims, 1 Drawing Sheet

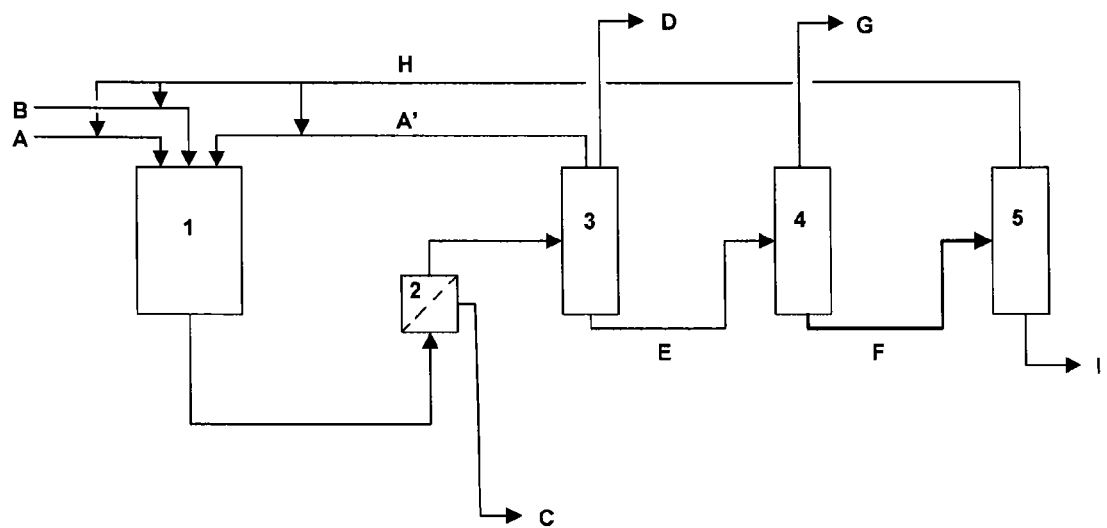

PRODUCTION OF TRISILYLAMINE FROM MONOCHLOROSILANE AND AMMONIA BY USE OF INERT SOLVENT

BACKGROUND OF THE INVENTION

1. Field of the Invention

The present invention relates to a process for producing trisilylamine from monochlorosilane and ammonia in the liquid phase. The present invention further relates to a plant wherein such a process can be carried out.

2. Discussion of the Background

Trisilylamine (TSA), $N(SiH_3)_3$, is an extremely mobile, colourless, self-ignitable and readily hydrolyzable liquid having a melting point of $-105.6°$ C. and a boiling point of $+52°$ C. Nitrogen-containing silicon compounds such as trisilylamine are important substances in the semiconductor industry.

It has long been known to use TSA to produce silicon nitride layers (U.S. Pat. No. 4,200,666, JP 1986-96741). TSA more particularly finds application in chip manufacture as a layer precursor for silicon nitride or silicon oxynitride layers. EP 1 547 138 for example discloses a very specific process for using TSA. Owing to its use in chip manufacture, it is important to be able to produce trisilylamine in the required, generally ultrapure quality in a safe, reliable and consistent manner.

Trisilylamine is synthesizable from monochlorosilane and ammonia as per the following equation:

$$3H_3SiCl + 4NH_3 \rightarrow N(SiH_3)_3 + 3NH_4Cl \quad (1)$$

Ammonium chloride is by-produced. The reaction of monochlorosilane and ammonia is a spontaneous, exothermic reaction.

Alfred Stock and Karl Somieski in Ber. Dtsch. Chem. Ges. 54, 740 ff., 1921, report the immediate reaction of monochlorosilane gas and ammonia gas at room temperature in accordance with equation (1). The reaction proceeds with excess monochlorosilane to produce quantitative trisilylamine. By-produced ammonium chloride separates out.

WO 2010/141551 describes the reaction of monochlorosilane with ammonia in the gas phase. WO 2011/049811 teaches producing silylamines as closely as possible to the site of use in order to minimize the delivery distance and hence the delivery time. According to WO 2011/049811, TSA-containing silylamines are obtainable from monochlorosilane and ammonia both in the gas phase and in the liquid phase.

US 2011/0178322 describes a process for producing trisilylamine by thermal decomposition of perhydropolysilazanes in an oxygen-free or low-oxygen atmosphere.

Richard L. Wells and Riley Schaeffer in J. Am. Chem. Soc. 88, 37 ff., 1966, already describe reacting monochlorosilane with ammonia by warming a mixture of the two compounds from $-196°$ C. to room temperature. In addition to trisilylamine formation as per equation (1), a sequence of descendent reactions is observed:

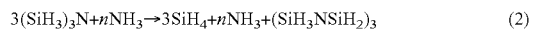

$$3(SiH_3)_3N + nNH_3 \rightarrow 3SiH_4 + nNH_3 + (SiH_3NSiH_2)_3 \quad (2)$$

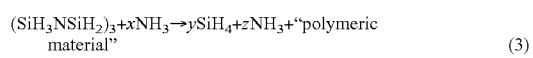

$$(SiH_3NSiH_2)_3 + xNH_3 \rightarrow ySiH_4 + zNH_3 + \text{"polymeric material"} \quad (3)$$

Thus, trisilylamine can react further in the presence of ammonia to form monosilane ($SiH_4$) and N,N',N''-trisilylcyclotrisilazane $(SiH_3NSiH_2)_3$ and also "polymeric material". Descendent reactions (2) and (3) have a disadvantageous effect on the yield of trisilylamine.

SUMMARY OF THE INVENTION

The problem addressed by the present invention was therefore that of providing a technical and very economical solution for liquid-phase production of trisilylamine from ammonia and monochlorosilane whereby product streams are interconnected within a multi-stage plant such that the conversion of the reactant feeds into the trisilylamine end product is very efficient.

This problem is solved according to the present invention by the features in the claims. What follows is accordingly a description of a process according to the present invention and of a plant according to the present invention, in which such a process can be carried out with advantage, including preferred embodiments.

BRIEF DESCRIPTION OF DRAWINGS

FIG. 1 shows the continuous production of TSA of the present invention in the form of a process scheme.

DETAILED DESCRIPTION OF THE INVENTION

It was surprisingly found that advantageous monochlorosilane (A and A') is initially charged to a reactor (1) in the liquid form of a solution in a solvent and ammonia (B), dissolved in the solvent, is passed into the reactor to obtain a product mixture containing TSA and $NH_4Cl$, which is in solid form. Subsequently, the resultant product mixture is routed out of reactor (1) via a filter unit (2) wherein solid ammonium chloride (C) is removed from the product mixture. Thereafter, the filtrate is fed into the distillation column (3) in which excess monochlorosilane (A') is distilled overhead, condensed, dissolved in the solvent and advantageously fed back into reactor (1) in liquid form. This solvent is inert with regard to monochlorosilane, ammonia as well as TSA and has a higher boiling point than TSA has. This solvent is preferably toluene.

It is further possible to remove monosilane (D) from the distillation column (3) overhead. The bottoms (E) of column (3) are conveyed into distillation column (4) where the product trisilylamine (G) is distilled overhead and condensed. Higher boilers are exported via the bottoms (F) and fed to column (5). The solvent is distilled in column (5) overhead, condensed and returned to the reactor feedstreams (A), (A'), (B) as a solvent.

The feeding of toluene (H) into the reactor feedstreams in the process of the present invention has the advantage of stopping monochlorosilane (A or A') and ammonia (B) from reacting with each other prematurely in the feed lines and causing the feed lines to plug by precipitation of ammonium chloride (C). Furthermore, TSA is stable in toluene (H). Toluene (H) further serves to dilute the reactor solution and to absorb reaction enthalpy. Moreover, ammonium chloride (C) is only sparingly soluble in toluene (H), facilitating the removal of ammonium chloride (C) by filtration.

Use of monochlorosilane and solvent as a mixture is advantageous in the process of the present invention, especially when the solvent is present in a volume-based excess relative to monochlorosilane. The solvent-to-monochlorosilane ratio between the volumes of the liquids is preferably in the range from 30:1 to 1:1, more preferably in the range from 20:1 to 3:1 and even more preferably in the range from 10:1 to 3:1. Admittedly, the advantages become smaller at volume ratios in the range from 3:1 to 1:1.

Ammonia ($NH_3$) can then be metered, suitably in a gaseous or liquid form, in solvent into the monochlorosilane-containing solution and be allowed to react, preferably while mixing/stirring. The molar stoichiometric quantity of monochlorosilane at this stage has to be at least equal to the molar stoichiometric quantity of ammonia. Preferably, monochlorosilane is present in a molar stoichiometric excess with regard to ammonia, or the reaction becomes highly unselective, the increased formation of polysilazanes is likely and TSA is decomposed by the action of $NH_3$.

The process of the present invention can be carried out both batchwise and continuously. In the case of a batchwise production of TSA, the reaction mixture can be decompressed in a reactor and the resultant product mixture worked up by distillation, preferably via at least two distillation stages. Ammonium chloride remaining behind in the reactor can be drained off underneath the reactor and discarded. FIG. 1 depicts the continuous production of TSA as per the claimed process in the form of a process scheme. Ammonium chloride can be filtered off in the case of continuous production.

The continuous process advantageously also allows recycling. As depicted in FIG. 1, MCS is condensed at the top of the first column and fed into the reactor in admixture with the solvent, preferably toluene. This solvent is condensed at the top of the third column and likewise returned into the reactor. Very pure TSA is obtained in the process of the present invention as a result.

The present invention accordingly provides a process for production of trisilylamine in the liquid phase, which process comprises initially charging monochlorosilane (A or A') to a reactor (1) in the liquid form of a solution in a solvent (H), wherein the solvent is inert with regard to monochlorosilane, ammonia as well as TSA and has a higher boiling point than TSA has, and passing ammonia (B) into the reactor in the form of a solution in the solvent (H), performing the reaction in reactor (1), subsequently passing the resultant product mixture from reactor (1) into and through a filter unit (2) and removing solid ammonium chloride (C) from the product mixture, and passing the filtrate from the filter unit (2) into the distillation column (3), excess monochlorosilane (A') being distilled in distillation column (3) overhead, condensed and fed to reactor (1) in liquid form under admixture of the solvent, and also removing gaseous substances (D), such as monosilane, from the distillation column (3) overhead, and conveying the bottoms (E) into the distillation column (4), the product trisilylamine (G) being distilled in the distillation column (4) overhead and condensed, and conveying the bottoms (F) into the distillation column (5), the solvent (H) being distilled in distillation column (5) overhead, condensed and returned to the reactor feedstreams (A), (A'), (B) as a solvent, and exporting higher boilers via the bottoms (I).

The reaction is preferably carried out under protective gas, for example nitrogen and/or a noble gas, preferably argon, and in the absence of oxygen and water (humidity, moisture), and the present plant is suitably dried and purged with protective gas before the first filling operation.

It is preferable to use a solvent (H) which does not form an azeotrope with TSA and more preferably has a boiling point which is at least 10 K higher than that of trisilylamine. Toluene is particularly preferred for use as solvent.

Moreover, the plant components used according to the present invention, which come into contact with substances occurring here, are advantageously made of stainless steel and are coolable/heatable in a controlled manner.

The process of the present invention preferably utilizes component (A or A') in a molar stoichiometric excess relative to component (B), while reactor (1) is suitably filled with the reaction mixture of components (A), (B), (A') recycled from distillation column (3) and also (H) as solvent up to 99%, preferably from 5 to 95% and more preferably from 20 to 80% of the reactor volume to perform the reaction. Advantageously, the monochlorosilane is initially charged for this in the liquid form of a solution in the inert solvent and ammonia is passed into this solution of monochlorosilane and the solvent, which is toluene with particular preference. Ammonia can be added in gaseous form or in the liquid form of a solution in the solvent.

It is further advantageous for the reactor contents to be mixed in the practice of the process according to the present invention, especially in the course of the reactor being filled and also in the course of reacting the components. The reaction or product mixture in reactor (1) can be stirred for instance.

The temperature at which the conversion of the reaction mixture in reactor (1) is carried out is advantageously in the range from −60 to +40° C., preferably in the range from −20 to +10° C., more preferably in the range from −15 to +5° C. and most preferably in the range from −10 to 0° C. The reaction can be carried out at a pressure of 0.5 to 15 bar, in particular under the autogenous pressure of the predetermined reaction conditions.

Furthermore, owing to the initial charging of liquid monochlorosilane, dissolved in the solvent, the reaction in the reactor establishes essentially the vapour/liquid equilibrium pressure of a corresponding mixture of monochlorosilane, the resultant trisilylamine and also any proportionate by-products in the solvent. Ammonia plays no part in the vapour/liquid equilibrium pressure, since ammonia fully reacts directly with the monochlorosilane (which is present in excess) on being passed into it.

The present invention further provides a plant in which the process of the present invention can be carried out, said plant comprising a reactor (1) with feeds for the reactants or components (A), (A'), (B) and also (H) as solvent and a product mixture outlet opening into a filter unit (2) which is connected to reactor (1) at the downstream end thereof and which in turn is equipped with a solids outlet for component (C) and with a line for conveying the filtrate out of unit (2) into a subsequent distillation unit which consists of at least three distillation columns (3), (4) and (5) and the distillation column (3) is equipped with an outlet overhead for a gaseous stream (D) and with an outlet overhead with a return line for condensed monochlorosilane (A') into the reactor (1) under admixture of solvent (H) and also with a line for transferring bottoms (E) from the distillation column (3) into the subsequent distillation column (4) to recover trisilylamine (G) and also with a line for transferring bottoms (F) from the distillation column (4) into the subsequent distillation column (5) to recover solvent (H) and also export bottoms (I).

The solvent (H) is inert with regard to monochlorosilane, ammonia as well as TSA and has a higher boiling point than TSA has. This solvent is preferably toluene.

The process according to the present invention is generally carried out in a plant according to the present invention by liquid monochlorosilane (A or A') and ammonia (B) being passed into a reactor (1), each with the solvent, preferably toluene, and suitably mixed to form a product mixture containing TSA and solid NH₄Cl. The product mixture is subsequently routed via a filter unit (2) in which solid ammonium chloride (C) is separated off. The filtrate from filter unit (2) is passed to a distillation column (3) in which excess monochlorosilane (A') is distilled overhead, condensed and fed back to reactor (1) in liquid form under admixture of the solvent, i.e. advantageously is recycled. Monosilane (D) can further be withdrawn from distillation column (3) overhead. The bottoms (E), which generally contains TSA, the solvent as well as higher boilers, is conveyed into column (4) in which very pure trisilylamine (G) can be distilled overhead, condensed and withdrawn. Higher boilers (F) are conveyed into column (5) in which the solvent (H) can be distilled overhead, condensed and recycled. Higher boilers (I) can be exported via the bottoms of column (5).

The present invention thus provides a simple and economical way to produce trisilylamine in industrial quantities and very good quality.

LIST OF REFERENCE NUMERALS (1) reactor
(2) filter unit
(3) distillation column
(4) distillation column
(5) distillation column
(A) monochlorosilane
(A') recycled monochlorosilane
(B) ammonia
(C) ammonium chloride
(D) gaseous substances overhead from (3), inter alia monosilane
(E) transfer of bottoms from (3) to (4)
(F) bottoms from (4)
(G) trisilylamine
(H) solvent
(I) bottoms from (5)

The invention claimed is:

1. A plant for reacting at least monohalosilane (A) and/or recycled monosilane (A'), and ammonia (B) in a solvent (H) in the liquid phase to form a product mixture for production of trisilylamine, said plant comprising:
   a) a stirred reactor equipped with liquid feed lines for the components (A) as solution in (H), and (A') as solution in (H), a feed line for (B), optionally as a solution in (H) and a bottom liquid product mixture outlet opening into
   b) a filter unit which is connected to said reactor at the downstream end thereof and which in turn is equipped with a solids outlet for ammonium chloride (C) and with a line for conveying a filtrate out of said filter unit into
   c) a subsequent distillation unit which comprises at least three distillation columns and a first distillation column of said at least three distillation columns is equipped with an outlet overhead for a gaseous stream (D) and with an outlet overhead with a return line for condensed recycled monochlorosilane (A') into the reactor under admixture of solvent (H) and also with a line for transferring bottoms (E) from the first distillation column of said at least three distillation columns into a subsequent second distillation column of said at least three distillation columns to recover trisilylamine (G) and also with a line for transferring bottoms (F) from the second distillation column of said at least three distillation columns into a subsequent third distillation column of said at least three distillation columns to recover solvent (H) and also export bottoms (I);
   wherein the solvent (H) is toluene; and
   wherein component (A) and/or (A') is used in a molar stoichiometric excess relative to component (B).

2. The plant according to claim 1, wherein the reactor is filled with the reaction mixture of components (A) and/or (A'), (B) and (H) up to 99% of the reactor volume to perform the reaction.

3. The plant according to claim 1, wherein the reaction in the reactor is carried out at temperature of −60 to +40° C.

4. The plant according to claim 1, wherein the process is carried out batchwise.

5. The plant according to claim 1, wherein the process is carried out continuously.

6. The plant according to claim 1, which is dried and purged with protective gas before a first filling operation with said reactants and/or said solvent.

7. The plant according to claim 1, wherein a plant component which comes into contact with any reaction component in said process comprises stainless steel.

8. The plant according to claim 1, wherein a plant component which comes into contact with any reaction component in said process is coolable and/or heatable in a controlled manner.

9. A plant for reacting at least monohalosilane (A) and/or recycled monosilane (A'), and ammonia (B) in a solvent (H) in the liquid phase to form a product mixture for production of trisilylamine, said plant comprising:
   a) a stirred reactor equipped with liquid feed lines for the components (A) as solution in (H), and (A') as solution in (H), a feed line for (B), optionally as a solution in (H) and a bottom liquid product mixture outlet opening into
   b) a filter unit which is connected to said reactor at the downstream
   end thereof and which in turn is equipped with a solids outlet for ammonium chloride (C) and with a line for conveying a filtrate out of said filter unit into
   c) a subsequent distillation unit which comprises at least three distillation columns and a first distillation column of said at least three distillation columns is equipped with an outlet overhead for a gaseous stream (D) and with an outlet overhead with a return line for condensed recycled monochlorosilane (A') into the reactor under admixture of solvent (H) and also with a line for transferring bottoms (E) from the first distillation column of said at least three distillation columns into a subsequent second distillation column of said at least three distillation columns to recover trisilylamine (G) and also with a line for transferring bottoms (F) from the second distillation column of said at least three distillation columns into a subsequent third distillation column of said at least three distillation columns to recover solvent (H) and also export bottoms (I);
   wherein said solvent is toluene;
   wherein a solvent-to-monochlorosilane ratio between the volumes of the liquids is in the range from 30:1 to 1:1;
   wherein the monochlorosilane is present in a molar stoichiometric excess to the ammonia;
   wherein the trisilylamine is formed at a temperature of −60 to +40° C.

* * * * *